US 7,416,734 B2

(12) United States Patent
Leonard et al.

(10) Patent No.: US 7,416,734 B2
(45) Date of Patent: Aug. 26, 2008

(54) **VACCINES FOR *MYCOPLASMA BOVIS* AND METHODS OF USE**

(75) Inventors: Joan D. Leonard, Olathe, KS (US); Robert W. Tully, Olathe, KS (US)

(73) Assignee: Biomune, Lenexa, KS (US)

( * ) Notice: Subject to any disclaimer, the term of this patent is extended or adjusted under 35 U.S.C. 154(b) by 324 days.

(21) Appl. No.: 10/825,391

(22) Filed: Apr. 14, 2004

(65) Prior Publication Data

US 2005/0118200 A1 Jun. 2, 2005
US 2008/0069842 A9 Mar. 20, 2008

Related U.S. Application Data

(62) Division of application No. 10/726,029, filed on Dec. 2, 2003, which is a division of application No. 09/708,352, filed on Nov. 8, 2000.

(60) Provisional application No. 60/164,286, filed on Nov. 8, 1999.

(51) Int. Cl.
*A61K 39/02* (2006.01)
*A61K 39/00* (2006.01)
*A61K 39/295* (2006.01)
*A61K 39/116* (2006.01)
*A61K 38/00* (2006.01)

(52) U.S. Cl. ............... 424/264.1; 424/184.1; 424/201.1; 424/202.1; 424/203.1; 530/300; 530/324

(58) Field of Classification Search ............... 424/184.1, 424/234.1, 264.1, 93.1; 435/41; 530/300, 530/324
See application file for complete search history.

(56) References Cited

U.S. PATENT DOCUMENTS

| | | | |
|---|---|---|---|
| 4,517,304 A | 5/1985 | Stott et al. | |
| 4,981,684 A | 1/1991 | MacKenzie et al. | |
| 5,178,860 A | 1/1993 | MacKenzie et al. | |
| 5,338,543 A | 8/1994 | Fitzgerald et al. | |
| 5,565,205 A | 10/1996 | Petersen et al. | |
| 5,585,098 A | 12/1996 | Coleman | |
| 5,665,363 A | 9/1997 | Hansen et al. | |
| 5,968,525 A | 10/1999 | Fitzgerald et al. | |
| 6,548,069 B2 * | 4/2003 | Hymas et al. ............ | 424/201.1 |

FOREIGN PATENT DOCUMENTS

DE 29921392 U1 12/1998

OTHER PUBLICATIONS

Stott et al (The Veterinary Record, Oct. 10, 1987).*
Poumarat et al, (Veterinary Microbiology, vol. 40, 1994, p. 305-321).*
Gourlay et al (Res Vet Sci., Sep. 1979, 27; 233-7).*
Chima et al, (Veterinary Microbiology vol. 5, pp. 113-122, (1980).*
Rawadi (G.A., Characterization of Mycoplasmas by RAPD Fingerprinting, Methods in Molecular Biology, 104:179-187.*
Amon R (Ed.), "Synthetic Vaccines I" CRC Press, Inc., Boca Raton. Florida, 83-92, 1987.
Artiushin et al., Arbitrarily Primed PCR Analysis of *Mycoplasma hyopneumoniae* Field Isolates Demonstrates Genetic Heterogeneity. Int Journal of Systematic Bacteriology, 46:324-328 (1996).
Al-Aubaidi et al., Characterization and Classification of Bovine Mycoplasma, Cornell University, Ithica, New York 490-518 (1970).
Behrens et al., A newly identified immundominant membrane protein (pMB67) involved in *Mycoplasma bovis* surface antigenic variation, *Microbiology* 142:2463-70 (1996).
Beier et al., Intraspecies polymorphism of vsp genes and expression profiles of variable surface protein antigens (Vsps) in field isolates of *Mycoplasma bovis*, Veterinary Microbiology 63:189-203 (1998).
Boothby et al., Experimental Intramammary Inoculation with *Mycoplasma bovis* in Vaccinated and Unvaccinated Cows: Effect on Milk Production and Milk Quality, Cornell Vet. 50: 200-204 (1986).
Boothby et al., Prevalence of mycoplasmas and immune responses to *Mycoplasma bovis* in feedlot calves, Am. J. Vet. Res. 44(5):831-838 (1983).
Boothby et al., Experimental Intramammary Inoculation with *Mycoplasma bovis* in Vaccinated and Unvaccinated Cows: Effect on Local and Systemic Antibody Response, Can. J. Vet. Res. 51:121-125 (1987).
Boothby et al., Immune Responses to *Mycoplasma bovis* Vaccination and Experimental Infection in the Bovine Mammary Gland, Can J Veterinary Research 52:355-359 (1988).
Boothby et al., Experimental Intramammary Inoculation with *Mycoplasma bovis* in Vaccinated and Unvaccinated Cows: Effect on the Mycoplasmal Infection and Cellular Inflammatory Response, Cornell Vet. 76(2): 188-197 (1986).
Boothby J.T., Immunologic Responses to *Mycoplasma bovis*. University Microfilms International (Dissertation) 1-172 (1982).
Boothby et al., Detecting *Mycoplasma bovis* in milk by enzyme-linked immunosorbent assay, using monoclonal antibodies, Am J Vet Re, 47, (5):1082-1084 (1986).

(Continued)

*Primary Examiner*—N. M. Minnifield
*Assistant Examiner*—Vanessa L. Ford
(74) *Attorney, Agent, or Firm*—Kenyon & Kenyon LLP (57) ABSTRACT

The invention of novel, effective vaccines against *Mycoplasma bovis* for use in cattle is described. These vaccines demonstrate no undesirable side effects and protect against *M. bovis* related disease, such as contagious mastitis, respiratory pneumonia, joint infections, keratoconjunctivitis and middle ear infections. The novel vaccines also lessen the effect of *M. bovis* infections on milk production, weight gain and animal health. Methods of diagnosing, characterizing and treating *M. bovis* infections as specific biotypes are also disclosed. Vaccine compositions made in accordance with the invention may be either of the attenuated or inactivated variety. Vaccines may also include antigens from other pathogens so as to provide a protective immunogenic response to diseases other than those caused by *M. bovis*.

11 Claims, 2 Drawing Sheets

OTHER PUBLICATIONS

Butler et al., Use of arbitrarily primed polymerase chain reaction to investigate *Mycoplasma bovis* outbreaks, Veterinary Microbiology 78:175-181 (2001).

Chima et al., Immunoprophylaxis of Experimental *Mycoplasma bovis* Arthritis in Calves. Protective Efficacy of Live Organisms and Formalinized Vaccines, Veterinary Microbiology, 5:113-122 (1980).

Cox et al., Adjuvants—a classification and review of their modes of action, Vaccine 15(3):248-256 (1997).

Fan et al., Application of Polymerase Chain Reaction with Arbitrary Primers to Strain Identification of *Mycoplasma gallisepticum*, Avian Diseases 39: 729-735 (1995).

Fan et al., Studies of Intraspecies Heterogeneity of *Mycoplasma synoviae, M. meleagridis*. and *M. iowae* with Arbitrarily Primed Polymerase Chain Reaction, Avian Diseases 37:766-777 (1995).

Geary et al., Inflammatory Toxin from *Mycoplasma bovis*: Isolation and Characterization, Science 212: 1032-1033 (1981).

Ghadersohi et al., Development of a specific DNA Probe and PCR for the detection of *Mycoplasma bovis*. Veterinary Microbiology, 56:87-98 (1997).

Hanson, M., *Mycoplasma mastitis*: It's everyone's problem, Bovine Veterinarian 4-8 (Sep. 2001).

Hanson, M., *Mycoplasma mastitis*: Prevention and control. Bovine, Veterinarian 12-20 (Oct. 2001).

Heller et al., Antigen capture ELISA using a monoclonal antibody for the detection of *Mycoplasma bovis* in milk, Veterinary Microbiology, 37:127-133 (1993).

Howard et al., Protection against respiratory disease in calves induced by vaccines containing respiratory syncytial virus bovis parainfluenza type 3 virus, *Mycoplasma bovis* and *M dispar*, The. Veterinary Record 121:372-376 (1987).

Howard et al., Immune Response of Cattle to Respiratory Mycoplasmas, Vet. Immunology & Immunopatology.17: 401-412 (1987).

Howard et al., Immune Responses to Mycoplasma Infections of the Respiratory Tract, Vet. Immunology & Immunopathology 10:3-32 (1985).

Howard et al., Immune Response of Calves Following the Inoculation of *Mycoplasma dispar* and *Mycoplasma bovis*, Veterinary Microbiology 8:45-56 (1983).

Howard et al., Immunity to *Mycoplasma bovis* infections of the respiratory tract of calves, Research in Veterinary Science 28:242-249 (1979).

Jasper D.E., The role of Mycoplasma in bovine mastitis, J Amer Vet Med Assn 181:158-162 (1982).

Kirk et al., Epidemiologic analysis of *Mycoplasma* spp isolated from bulk-tank milk samples obtained from dairy herds that were members of a milk cooperative, J Am Vet Med Assoc 211(8):1036-1038 (1997).

Knudtson et al., Identification of Mycoplasmatales in Pneumonic Calf Lungs, Vet Microbiol 11:79-91 (1986).

Kunkel, J.R., Isolation of *Mycoplasma bovis* from Bulk Milk, Cornell Vet. 75:398-400 (1985).

Pettersson et al., Phylogeny of Some Mycoplasmas from Ruminants Based on 16S rRNA Sequences and Definition of a New cluster within the Hominis Group, Int Journal of Systematic Bacteriology 46(4):1093-1098 (1996).

Poumarat et al., Genomic, protein and antigenic variability of *Mycoplasma bovis*, Vet Microbiol. 40:305-321 (1994).

Poumarat et al., Efficacy of spectinomycin against *Mycoplasma bovis* induced pneumonia in conventionally reared calves, Veterinary Microbiology 80:23-35 (2001).

Raspberry et al., Membrane-Associated and Cytosolic Species-Specific Antigens of *Mycoplasma bovis*, Recognized by Monoclonal Antibodies, Hybridoma 14 (5):481-485 (1995).

Rawadi, G.A., Characterization of Mycoplasmas by RAPD Fingerprinting, Methods in Molecular Biology 104:179-187.

Razin et al., DNA Cleavage Patterns as Indicators of Genotypic Heterogeneity among Strains of *Acholeplasma* and *Mycoplasma* Species, Journal of General Microbiology 129:1935-1944 (1983).

Rosenbusch et al., Test of an Inactivated Vaccine Against *Mycoplasma bovis* Respiratory Disease by Transthoracic Challenge with an Abscessing Strain, Abstract G07, 17th International Organization of Mycoplasmology, AU Tech Park, Sydney, AU Jul. 22-28, 1998.

Sachse et al., Comparison Between Different Diagnostic Methods for the Detection of *Mycoplasma bovis*, Rev Sci Tech 12(2):576-577 (1993).

Stott et al., Field trial of a quadrivalent vaccine against calf respiratory disease, The Veterinary Record 121:342-347 (1987).

Subramaniam et al., Species identification of *Mycoplasma bovis* and *Mycoplasma agalactiae* based on the uvrC genes by PCR, Molecular Cellular Probes 12:161-169 (1998).

Thomas et al., Development of a Multivalent Vaccine Against Calf Respiratory Disease, A.F.R.C. Institute for Research on Animal Diseases, Compton, Newbury, Berkshire U.K. 691-695.

Thoms et al., Res. Vet. Sci. 29 (3) 328-332. (1980).

Urbaneck et al., Experiences with Herd-Specific Vaccines against Respiratory Infections with *Mycoplasma bovis* in a Large Cattle Feedlot, Veterinary Practitioner 81(9): 756-763 (2000).

* cited by examiner

FIG. 1

FIG. 2 ial of co-pending prior U.S.
VACCINES FOR *MYCOPLASMA BOVIS* AND METHODS OF USE This application is a divisional of co-pending prior U.S. patent application Ser. No. 10/726,029 filed on Dec. 2, 2003, which is a divisional of U.S. patent application Ser. No. 09/708,352 filed on Nov. 8, 2000, which claims benefit of U.S. Patent Application Ser. No. 60/164,286, filed on Nov. 8, 1999.

FIELD OF THE INVENTION

This invention relates to novel vaccines for protection against *Mycoplasma bovis* disease in animals, compositions for the diagnosis of such infections, and methods of diagnosis and vaccination.

BACKGROUND OF THE INVENTION

*Mycoplasma bovis* is a pathogenic prokaryote belonging to a class of organisms that is intermediate in size between a bacteria and virus. These mycoplasmas are the smallest of the free-living microorganisms. They are characterized by the lack of a cell wall and are enveloped with only a cell membrane, which allows for varying morphological shapes and unique growth requirements.

Mycoplasmas are known to cause infectious disease in most species of animals. In bovine species, *Mycoplasma bovis* is an opportunistic microorganism that causes infectious disease that is of significant economic importance to the livestock industry. *Mycoplasma bovis* isolation in a diseased bovine can be the result of its role as either a primary or secondary causative etiological disease agent. Clinical disease and losses associated with infections caused by *Mycoplasma bovis* in beef and dairy cattle include: contagious mastitis, respiratory pneumonia, joint infections (arthritic conditions), keratoconjunctivitis, and middle ear infections. Even though several species of mycoplasmas have been isolated in cattle, by far the most prevalent is *Mycoplasma bovis*. For mastitis infections, the prevalence of *M. bovis* is reported to be 70% or more.

Diseases caused by mycoplasmas are often resistant to antimicrobial therapy, leaving no effective means of treatment. Consequently, the only effective control method is to cull animals from a herd. This has enormous economic implications in the dairy industry where losses are measured by the value of the culled animals as well as the impact on both milk quality and quantity due to clinical and subclinical infections. *Mycoplasma* infections resulting in bovine mastitis are increasing in prevalence and geographical distribution. In the United States, this higher prevalence is due to a larger and more intense cattle production industry in which herds are rapidly expanding, placing them at greater risk. Increased incidence of *M. bovis* infection and related infectious disease in dairy herds has been noted worldwide (Jasper, D E 1982, J. Amer. Vet. Med. Assn. 181:158-162).

Control of disease caused by mycoplasmas in swine and avian species has occurred in recent years as the result of successful vaccination programs using safe and efficacious products. The design and development of an effective commercial vaccine in the United States to control *Mycoplasma bovis* has not yet occurred, even though changes in cattle production methods and husbandry practices have resulted in a greater commercial need to control this agent from both an economic and food quality perspective. Although there have been numerous attempts to produce vaccine to protect against *Mycoplasma bovis*, the resulting experimental vaccines have been deemed unacceptable due to the lack of protection as well as unacceptable site reactions in vaccinated animals (Boothby, et al. 1986 Cornell Vet 76: 188-197; Boothby et al. 1987 Can J. Veterinary Research 51:121-125; Howard et al. 1987 Veterinary Record 121:372-376; Boothby, et al. 1988 Can J. Veterinary Research 52:355-359). Thus, there remains a need in the veterinary and animal health profession to provide a safe and effective vaccine to prevent infectious disease caused by *Mycoplasma bovis* with no unfavorable host animal reactions.

SUMMARY OF INVENTION

The invention disclosed herein provides safe and effective vaccines for the prevention of *Mycoplasma bovis* disease in cattle. Also disclosed are methods for characterizing biotypes of *Mycoplasma bovis* in cattle, bulk milk tanks, and barns.

DESCRIPTION OF FIGURES

FIG. 1 is an illustration of the gel electrophoretic pattern for DNA products produced by Polymerase Chain Reactions from different *Mycoplasma bovis* isolates. On the left side of the figure, molecular weight standards based on restriction endonuclease digests of lambda and phi phage are shown. The size of the bands in the standard digests are, from top to bottom, for lambda; n/d, n/d, n/d, 2027, 1904, 1584, 1375, 947, 831 and 564 base pairs, and for Phi X174; 1353, 1078, 872, 603, 310, 284/271, 234, 194 and 118 base pairs. The relative location of PCR-generated markers for different biotypes, designated A and B, are shown in lanes 5-12 to the right of the standards. Arrows in lanes 5 and 7 indicate the presence of three and two characteristic bands for biotypes A and B, respectively.

FIG. 2 is an illustration of the gel electrophoretic pattern for DNA products produced by Polymerase Chain Reactions from a second set of *Mycoplasma bovis* isolates. On the left side of the figure, molecular weight standards based on restriction endonuclease digests of lambda and phi phage are shown. The size of the bands in the standard digests are, from top to bottom, for lambda; n/d, n/d, n/d, 2027, 1904, 1584, 1375, 947, 831 and 564 base pairs, and for Phi X174; 1353, 1078, 872, 603 and 310 base pairs. The relative location of PCR-generated markers for different biotypes, designated A and C, are shown in lanes 5-11 to the right of the standards. Arrows in lanes 5 and 8 indicate the presence of the three and two characteristic bands for biotypes A and C, respectively.

DETAILED DESCRIPTION OF THE INVENTION

As used throughout the specification and in the claims, "a," "an" or "the" can mean one or more, depending upon the context in which it is used.

In accordance with the purposes of this invention, as embodied and broadly described herein, this invention, in one aspect, provides a vaccine composition which is protective against *Mycoplasma bovis* disease in a bovine species, comprising one or more inactivated or attenuated *Mycoplasma bovis* biotype(s) and a pharmaceutically acceptable excipient. The term "inactivated," also referred to as "killed," means that the microorganisms are treated by any of several means known to the art so that they no longer grow or reproduce, but that the microorganisms are still capable of eliciting an immune response in the target animal. Examples of inactivating agents are: formalin, azide, freeze-thaw, sonication, heat treatment, sudden pressure drop, detergent (especially nonionic detergents), lysozyme, phenyl, proteolytic enzymes, propiolactone, Thimerosal (see U.S. Pat. No. 5,338,543 Fitzgerald, et al.), and binary ethyleneimine (see U.S. Pat. No. 5,565,205 Petersen, et al.). In a specific embodiment, the *Mycoplasma bovis* strains used in the vaccine are inactivated with beta-propiolactone (BPL).

Alternatively, the *M. bovis* biotypes used in the vaccine can be attenuated. The term "attenuated," also referred to as "modified live," is intended to refer to a living biotype of *Mycoplasma bovis* which has been attenuated (modified) by any of a number of methods known in the art including, but not limited to, multiple serial passage, temperature sensitive attenuation, mutation, or the like such that the resultant strain is relatively non-pathogenic to a bovine species. The modified live strain should be capable of limited replication in the vaccinated animal and of inducing a protective immune response which is protective against disease caused by virulent or wild-type *Mycoplasma bovis*.

The term "pharmaceutically acceptable" means a material that is not biologically or otherwise undesirable, i.e., the material may be administered to an animal along with the immunogenic material (i.e. inactivated or attenuated *M. bovis* biotypes) without causing any undesirable biological effects or interacting in a deleterious manner with any of the other components of the vaccine in which it is contained. Examples of such pharmaceutically acceptable excipients include water and physiological saline (for further examples, see Arnon, R. (Ed.) *Synthetic Vaccines* I:83-92, CRC Press, Inc., Boca Raton, Fla., 1987).

The invention disclosed herein is based in part on the discovery that *Mycoplasma bovis* infections in the field comprise mixtures of biotypes. The term "biotype" means a variant of a species, i.e. a strain, that can be distinguished by one or more characteristics, such as ribosomal RNA sequence variation, DNA polymorphisms, serological typing, or toxin production (see e.g., Sambrook et al., *Molecular Cloning: A Laboratory Manual*, 2nd Ed., Cold Spring Harbor Laboratory, Cold Spring Harbor, N.Y., 1989; *DNA cloning: A Practical Approach*, Volumes I and II, Glover, D. M. ed., IRL Press Limited, Oxford, 1985; Harlow and Lane, *Antibodies, A Laboratory Manual*, Cold Spring Harbor Publications, N.Y. (1988)).

In another aspect of this invention, to produce an effective vaccine against *Mycoplasma bovis*, the vaccine must contain antigen derived from a biotype of *Mycoplasma bovis*. Examples of specific embodiments would include vaccines containing antigen derived from *M. bovis* biotypes A, B, or C. In a further specific embodiment, the vaccine comprises antigen derived from more than one *M. bovis* biotypes (e.g., A and B, A and C, B and C, or A, B and C). In a further specific embodiment, the vaccine comprises antigen derived from one or more *M. bovis* biotypes and antigen derived from another pathogen. In a further specific embodiment, the vaccine comprises inactivated or attenuated *M. bovis* biotype A, B or C. In a further specific embodiment, the vaccine comprises at least two inactivated or attenuated *M. bovis* biotypes (e.g., A and B, A and C, B and C, or A, B and C). In a further specific embodiment, the vaccine comprises at least one inactivated or attentuated *M. bovis* biotype with antigen derived from another pathogen. In a preferred embodiment, the vaccine comprises inactivated or attenuated *M. bovis* biotype A, as defined herein, and at least one other biotype of *M. bovis*.

It is anticipated that additional biotypes of *M. bovis* may emerge and may be isolated with continued animal production. Additional biotypes can be added to the vaccine as needed. It is a matter of routine practice to sample bulk milk tanks and blood from cows to isolate *Mycoplasma bovis* cultures. These cultures can then be biotyped according to any of several typing techniques, as listed hereinabove. Vaccines can be formulated based on the prevalence of *M. bovis* biotypes present in the environment. Autogenous vaccines, i.e. those vaccines for use on the farm where the microorganisms are isolated, can be custom-designed to contain all biotypes found on the farm, but not any other biotype. Vaccines developed for use by a mass market, i.e. those vaccines produced for general use on many different farms containing pre-selected biotypes, can also be developed, marketed and used.

In another aspect, this invention provides a vaccine comprising a single, inactivated or attenuated *Mycoplasma bovis* biotype, a pharmaceutically acceptable excipient, and a suitable adjuvant. In a specific embodiment, the vaccine contains inactivated or attenuated *M. bovis* biotypes A, B or C or any mixture thereof and may further contain antigens from other pathogens.

In a preferred embodiment, the inactivated vaccines of this invention are produced from biotypes freshly isolated from infected animals or from cryopreserved biotype cultures freshly prepared from infected animals. In a preferred embodiment, the attenuated vaccines of this invention are produced from cultures of biotypes which have been treated so as to retain a limited ability to replicate within the vaccinated animal, but which does not retain the ability to infect other animals and cause mycoplasma-related disease. The preparation and use of attenuated vaccines is well-known to practitioners of ordinary skill in the art.

The inactivated or attenuated *M. bovis* biotype(s) may be further processed to fractionate and/or standardize the antigenic mass. For example, specific biotypes might be isolated from samples and combined to form specific combinations of biotypes in specific ratios. Similarly, components from a specific inactivated or attentuated *M. bovis* biotype might be fractionated and a subset of those fractions combined with similarly fractionated components of another biotype to standardize the antigenic component of the vaccine preparation and to optimize its efficacy. In one embodiment, the antigenic components derived from a single biotype are enriched by removing non-immunogenic components from the cells of the biotype. In another embodiment, the vaccine preparations are standardized to provide a required minimum cell content per formulated dose. In a preferred embodiment, the vaccine comprising inactivated *M. bovis* biotype(s) is formulated to deliver at least $10^8$ *M. bovis* cell equivalents of each biotype per dose. A complete vaccination of a bovine species comprises the administration of recommended doses. In a preferred embodiment, two such doses will be administered. In a further preferred embodiment, three such doses will be administered. In another preferred embodiment, the vaccine comprising attenuated *M. bovis* biotype(s) is formulated to deliver at least $10^5$ *M. bovis* cells per biotype. It is understood by those skilled in the art that the critical value in describing a vaccination dose is the total amount of immunogen needed to elicit a protective response by the host animal to infectious disease caused by virulent or wild-type *M. bovis*. The number and volume of doses used can be varied and are determined by the practitioner based on costs and the need to avoid deleterious side effects in the animal caused by the administration. For example, the volume of one administration typically does not exceed 2-5 milliliters. The number of doses of inactivated vaccine needed in adult animals is typically one initial dose followed by 1-2 additional doses and annual revaccination. The number of doses of attenuated vaccine in adult animals is one initial dose followed by a booster. Subsequently, annual boosters are administered.

The vaccines of the present invention may further comprise antigenic material of other viruses and/or microorganisms known to be bovine pathogens, including, but not limited to, attenuated (modified-live) or inactivated viruses or microorganisms. Such combination vaccines provide protection against a plurality of diseases to which the bovine species are exposed, including but not limited to immunogenic compositions for *Staphylococcus aureus, Pasteurella hemolytica, Pasteurella multocida, Hemophilus somnus*, Bovine Respiratory Syncytial Virus, Bovine Diarrhea Virus, *E. coli* and Infectious Bovine Rhinotrachial Disease.

In other embodiments, the vaccine of this invention further comprises a suitable adjuvant. As used herein, an "adjuvant" is a potentiator or enhancer of the immune response. The term "suitable" is meant to include any substance which can be used in combination with the vaccine immunogen (i.e. inactivated or attenuated *M. bovis* biotypes or fractions thereof) to augment the immune response, without producing adverse reactions in the vaccinated animal. Effective amounts of a specific adjuvant may be readily determined so as to optimize the potentiation effect of the adjuvant on the immune response of an animal vaccinated. In a preferred embodiment, adjuvanting of the vaccines of this invention is a 2—stage process utilizing firstly a 2% aluminum hydroxide solution and secondly a mineral oil. In specific embodiments, suitable adjuvants can be chosen from the following group: mineral, vegetable or fish oil with water emulsions, incomplete Freund's adjuvant, *E. coli* J5, dextran sulfate, iron oxide, sodium alginate, Bacto-Adjuvant, certain synthetic polymers such as Carbopol (BF Goodrich Company, Cleveland, Ohio), polyamino acids and co-polymers of amino acids, saponin, carrageenan, REGRESSIN (Vetrepharm, Athens, Ga.), AVRIDINE (N,N-dioctadecyl-N',N'-bis(2-hydroxyethyl)-propanediamine), long chain polydispersed β (1,4) linked mannan polymers interspersed with O-acetylated groups (e.g. ACEMANNAN), deproteinized highly purified cell wall extracts derived from non-pathogenic strain of *Mycobacterium* species (e.g. EQUIMUNE, Vetrepharm Research Inc., Athens Ga.), Mannite monooleate, paraffin oil, and muramyl dipeptide.

In another aspect, this invention discloses a method for immunizing bovine animals against infectious disease caused by *Mycoplasma bovis* comprising administering to a bovine animal immunogenic amounts of inactivated or attenuated *Mycoplasma bovis* biotypes to elicit a protective immune response by the animal. Preferably, the method comprises administering at least two inactivated or attenuated *Mycoplasma bovis* biotypes to elicit a protective immune response by the animal. Immunization may be performed orally, intranasally, intratracheally, intramuscularly, intramammarily, subcutaneously, intravenously, or intradermally. The vaccine containing the inactivated or attenuated *M. bovis* biotypes can be administered by injection, by inhalation, by ingestion, or by infusion. Repeated doses of the vaccine preparations, i.e. "boosters", are preferable at periodic time intervals to enhance the immune response initially or after a long period of time since the last dose. The time interval between vaccinations varies depending on the age and condition of the animal. For lactating and adult animals, the first vaccination is preferably given at the end of the lactation cycle (i.e. "dry-off"), followed by a "booster" dose 2-4 weeks later, and preferably followed by a second booster dose 2-4 weeks thereafter. Newborn calves are preferably vaccinated at birth, followed by booster doses every 3-5 weeks until the calves are 4-6 months old and annually thereafter. However, at risk or exposed stocker and feeder animals should be vaccinated more often, preferably no less than once every 6 months.

In another embodiment of the methods of this invention, the multiple *M. bovis* biotypes comprising the vaccine can be delivered in separate administrations to the animal. For example, the vaccine comprising inactivated *M. bovis* biotypes A and B can be delivered by separately administering an immunogenic amount of biotype A in one injection and an immunogenic amount of biotype B in another injection. In a further embodiment, each separately administered biotype can be administered as a combination vaccination, comprising antigenic material of other viruses and/or microorganisms known to be bovine pathogens.

The term "immunogenic amount" means an amount of an immunogen, i.e. the inactivated or attenuated *M. bovis* biotype(s) or a portion thereof, which is sufficient to induce an immune response in a vaccinated bovine species and which protects the animal against disease caused by wild-type or virulent *M. bovis* infections upon exposure thereto or which has a commercially beneficial effect that lessens the effect of *M. bovis* on milk production, weight gain or animal health. In a preferred embodiment, bovine animals are immunized by administering at least approximately $10^8$ *M. bovis* cell equivalents of each inactivated biotype in the vaccine. In a specific embodiment, animals are immunized by administering at least approximately $10^8$ *M. bovis* biotype A cell equivalents and approximately $10^8$ *M. bovis* biotype B cell equivalents, which have been inactivated, in at least two injections. In another specific embodiment, bovine animals are immunized by administering at least approximately $10^8$ *M. bovis* biotype A cell equivalents, $10^8$ *M. bovis* biotype B cell equivalents and approximately $10^9$ *M. bovis* biotype C cell equivalents, which have been inactivated, in at least two injections.

In another preferred embodiment, bovine animals are immunized by administering at least approximately $10^5$ *M. bovis* cells of each attenuated biotype in the vaccine. In a specific embodiment, bovine animals are immunized by administering at least approximately $10^5$ *M. bovis* biotype A attenuated cells and at least approximately $10^5$ *M. bovis* biotype B attenuated cells. In another specific embodiment, bovine animals are immunized by administering at least approximately $10^5$ *M. bovis* biotype A cells, $10^5$ *M. bovis* biotype B cells, and $10^5$ *M. bovis* biotype C cells.

In another aspect, this invention discloses a method for producing a *Mycoplasma bovis* vaccine comprising contacting at least two live *Mycoplasma bovis* biotypes with an inactivating material and incorporating the inactivated *Mycoplasma bovis* biotypes into a pharmaceutically acceptable excipient with a suitable adjuvant to produce a *Mycoplasma bovis* vaccine. In a preferred method, selected *Mycoplasma bovis* biotypes are grown separately as pure cultures, free of contamination by viruses, bacteria or any other microbial agent, including other biotypes of M bovis, to the desired cell equivalents, inactivated as described herein, and then combined in equal amounts with a pharmaceutically acceptable excipient to produce a *Mycoplasma bovis* vaccine. Alternatively, the biotypes can be grown together as a mixed culture to the desired cell equivalents, inactivated and then, optionally, combined with a pharmaceutically acceptable excipient and a suitable adjuvant to produce a *Mycoplasma bovis* vaccine.

In a further embodiment of the hereinabove disclosed method of producing a *Mycoplasma bovis* vaccine, the inactivated or attenuated *Mycoplasma bovis* biotypes are mixed with a suitable adjuvant. In a preferred method, the suitable adjuvant is an aluminum hydroxide-oil emulsion.

Selected *M. bovis* biotypes may be used as the basis for diagnostic tools to detect the presence of *M. bovis*. In one aspect of this invention, samples from cattle would be tested for the presence of antibodies specific for *M. bovis* by contacting the samples with *M. bovis* cells or antigens derived from M bovis. Examples of technologies that could be adapted to such a method include, but are not limited to, RIA, ELISA and immunoblot. Examples of specific embodiments would include antigens derived from one or more *M. bovis* biotypes (e.g., A, B, C, A and B, B and C, A and C, or A, B and C). In a preferred embodiment, antigen from each of the M bovis biotypes A, B and C would be utilized to test for the presence of antibodies specific for each of the *M. bovis* biotypes, thus allowing an autogenous vaccine to be administered. In another embodiment, antibodies-raised against *M. bovis* biotypes or antigens-derived from selected biotypes would be used to test for the presence of *M. bovis* biotypes A, B and C. Examples of specific embodiments would include antibodies reactive to antigens derived from one or more *M. bovis* biotypes (e.g., A, B, C, A and B, B and C, A and C, or A, B and C). In another embodiment, antigens derived from different biotypes would be utilized to test for the presence of antibodies specific against antigens from a given biotype.

In a further embodiment, the present invention provides an isolated *Mycoplasma bovis* biotype A, *Mycoplasma bovis* biotype B, *Mycoplasma bovis* biotype C, or any combination thereof.

Throughout this application, various publications are referenced. The disclosures of these publications in their entireties are hereby incorporated by reference into this application in order to more fully describe the state of the art to which this invention pertains.

EXAMPLES

Example 1

Characterization and Typing of Field Isolates

Strains were collected from infected animals or milk tanks. Single colonies were cultured, and each culture was analyzed for cytotoxicity and for the presence of specific DNA markers by PCR fingerprinting.

PCR fingerprinting: Arbitrarily-chosen primers were selected; Primer 1 and Primer 2 below (I representing deoxyinosine and A, C, T and G representing the four naturally-occurring bases of DNA):

Primer 1: 5' III ICG ICG ICA TCI GGC 3'; [SEQ ID NO: 1] and

Primer 2: 5' ICG ICT TAT CIG GCC TAC 3'; [SEQ ID NO: 2]

*Mycoplasma bovis* DNA was isolated and amplified, using these primers, in a polymerase chain reaction (PCR) as follows: The initial cycling step was for 120 seconds at 94° C. Denaturation was for 30 seconds at 94° C., followed by annealing for 90 seconds at 40° C., extension for 120 seconds at 72° C., with a final extension for 240 seconds at 72° C. A total of 35 cycles of amplification were used.

The resulting DNA products of the PCR were separated by non-denaturing 1.5% agarose gel electrophoresis and were visualized by staining with ethidium bromide and illuminating the gel with a UV light source. Comparison of the resultant patterns, characteristic for a given biotype, with molecular weight standards such as the EcoRI/HindIII digest of lambda phage or the HaeIII digest of phiX174 phage, electrophoresed alongside the PCR products, allows consistent and reproducible biotyping of *M. bovis* strains. Examples of biotyping results using this method are provided below.

| Strain ID | Culture # | % Cytotoxicity | Biotype Profile |
|---|---|---|---|
| BA2580 | 1 | 95 | A |
|  | 2 | 0 | A |
| BA2491 | 1 | 82 | A |
|  | 2 | 100 | A |
| 498 | 1 | 100 | A |
|  | 3 | 91 | A |
| 4082 | 1 | 100 | B |
|  | 2 | 91 | B |
|  | 3 | 83 | B |
| Tank 2-18 | 1 | 90 | A |
|  | 2 | 100 | A |
|  | 3 | 100 | A |
| Tank 2-19 | 1 | 100 | A |
|  | 2 | 20 | A |
|  | 3 | 100 | A |
| L-56291 | 1 | 100 | A |
|  | 2 | 100 | A |
|  | 3 | 86 | A |
| L-477 | 1 | 84 | C |
|  | 2 | 76 | C |
|  | 3 | 90 | C |
| L-53219 | 1 | 66 | A |
|  | 2 | 100 | A |
|  | 3 | 100 | A |

Figure 1:
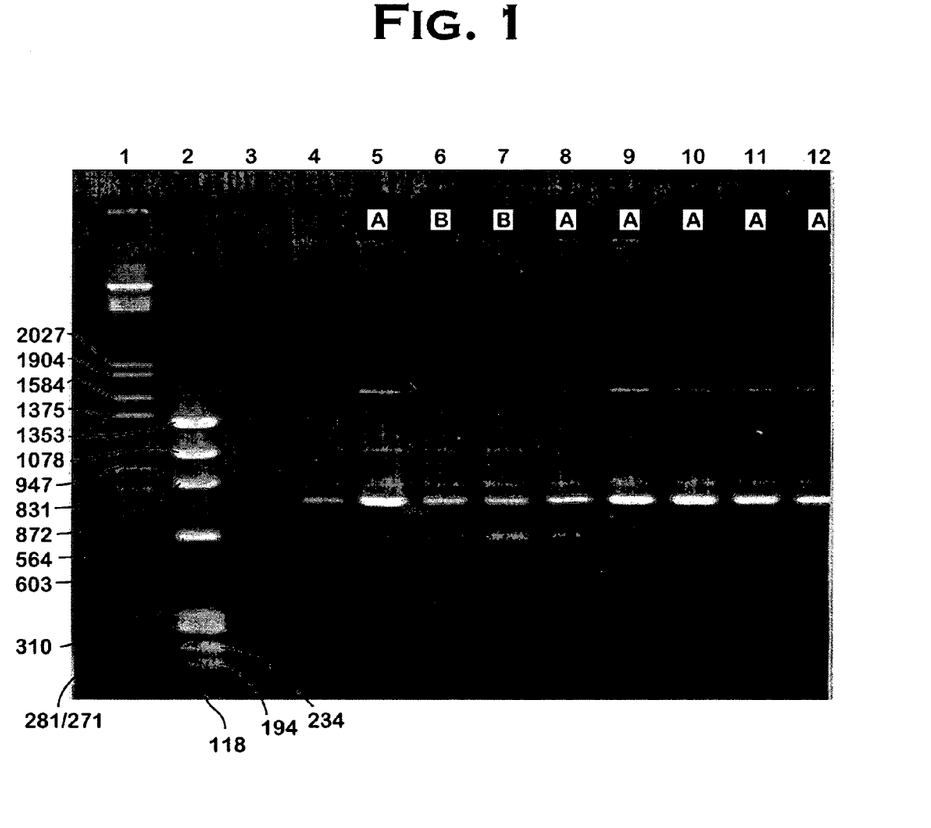
Figure 2:
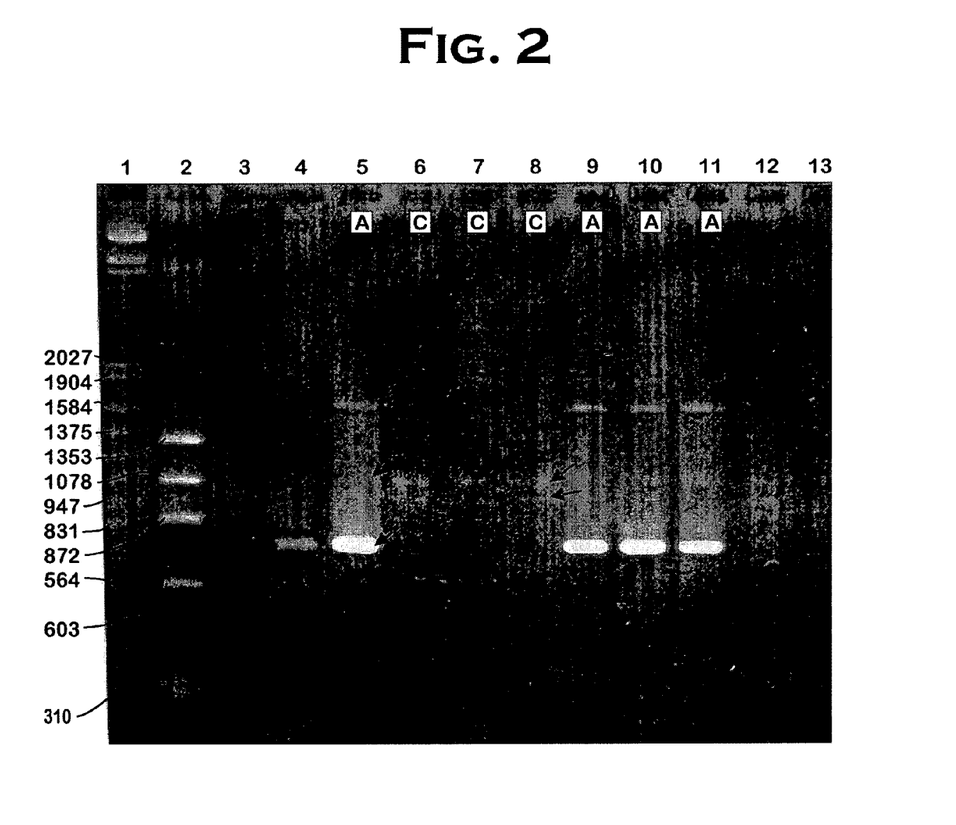

Both cytotoxic (i.e. ≧40% cytotoxic) and noncytotoxic strains are pathogenic. While the majority of isolates are homogeneously cytotoxic, a few isolates, e.g. BA2580 and Tank 2-19, are a mixture of non-cytotoxic and cytotoxic colonies. Following extensive passage in culture, all strains become noncytotoxic, while passage through calves accentuates the initial phenotype, whether non-cytotoxic or cytotoxic. The PCR fingerprints for three *M. bovis* biotypes are illustrated in FIGS. 1 and 2 alongside the standards formed by the EcoRI/HindIII restriction endonuclease digest of lambda phage and the HaeIII restriction endonuclease digest of phi phage. The sizes of the resultant standard fragments, in base pairs, are listed in the description of FIGS. 1 and 2. A blank and a positive control for the PCR fingerprinting reactions are included in lanes 3 and 4, respectively, for both FIGS. 1 and 2. Further description of PCR fingerprinting can be found in Artiushin et al. Int. J. Syst. Bacteriol. 46: 324-328 (1996), Fan et al. Avian Dis. 39: 729-735 (1995) and elsewhere. Other methods of biotyping mycoplasma, or other microorganisms, are well-known to the art and may also be used in the practice of the invention (see e.g., Sambrook et al., *Molecular Cloning: A Laboratory Manual*, 2nd Ed., Cold Spring Harbor Laboratory, Cold Spring Harbor, N.Y., 1989; *DNA cloning: A Practical Approach*, Volumes I and II, Glover, D. M. ed., IRL Press Limited, Oxford, 1985; Harlow and Lane, *Antibodies, A Laboratory Manual*, Cold Spring Harbor Publications, N.Y. (1988)).

Example 2

Preparation of an Inactivated Vaccine Against Biotypes of *Mycoplasma*

A *Mycoplasma bovis* vaccine is prepared by inactivating a selected biotype of *Mycoplasma bovis* and combining this preparation with an adjuvant.

A. Selection of *M. bovis* Biotypes

Isolates of *M. bovis* were obtained from samples of infected milk. These isolates were then cultured using standard techniques, such as those described by Knudtson et al. Vet. Microbiol. 11: 79-91 (1986).

Selected isolates were further expanded and characterized by biotype. Cultures of isolates representative of the characteristic biotypes, as determined by PCR fingerprinting, were selected and stocks of these biotypes were preserved by combining them with a gelatin protein hydrolysate stabilizing solution and subjecting the product to cryopreservation. Pure biotype cultures were used to inoculate a controlled fermentation of the microorganism for use in producing vaccine. PCR fingerprinting of these cultures for vaccine production confirmed their purity as single biotypes. Subsequent testing of the cryo-preserved stock(s) was performed in a USDA licensed facility according to Title 9 Code of Federal Regulations to validate purity and identity of the culture(s). Identity was determined to be *Mycoplasma bovis* by two independent laboratories when tested by indirect immunofluorescence with specific antisera to the following species:

*Mycoplasma bovis*
*Mycoplasma califoricum*
*Mycoplasma alkalescens*
*Mycoplasma canadense*
*Mycoplasma bovigenitalium*
*Mycoplasma bovirhinis*
*Mycoplasma arginnii*
*Acholeplasma laidlawii*

B. Propagation of the Pure, Isolated Biotypes

Selected strains, or biotypes, identified as being pure, were propagated in a defined media and further processed to make vaccines.

*Mycoplasma bovis* biotypes can be propagated in a variety of different general purpose, growth-promoting, defined media that are known to those knowledgable in the art, including, but not limited to, Hayflick Media, Adler Media, and Gourlay Media. In a preferred embodiment of this invention, the propagation medium is:

| | |
|---|---|
| Yeast Extract: | 5 grams per liter |
| Proteose Peptone: | 2 grams per liter |
| Mixed substrate Peptone, such as | |
| Enhancetone: | 20 grams per liter |
| Dextrose: | 2 grains per liter |
| Sodium Chloride: | 5 grams per liter |
| Sodium Phosphate: | 2.5 grams per liter |
| Glycerol: | 1 gram per liter |
| Nutrient | |
| Horse Serum: | 50 ml per liter |
| 1% NAD/Cysteine: | 20 ml per liter |
| Water: | to volume of 1000 ml |

Cultures were expanded and inoculated into media at a concentration of $10^7$-$10^8$ cfu/milliliter. Cultures were grown at a temperature between 30 and 41° C., under normal atmospheric oxygen pressure, with the percentage of $CO_2$ in the environment kept between 0% and 10%. Incubation times ranged from 8 hours to 72 hours. The endpoint of incubation is determined by the time at which the cultures reach stationary phase, as measured by standard microbiological methods.

Standard microbiological methods are used to determine immunogen mass, e.g. a direct plate count procedure or a spectophotometric optical density method based upon light absorbance of the *Mycoplasma bovis* cultured cell mass.

C. Inactivation of *Mycoplasma bovis*

Beta-propiolactone (BPL) is prepared as a 10% solution (v/v) in chilled water. The chilled solution is slowly added to the *M. bovis* culture(s) with constant stirring, thereby allowing hydrolysis. This BPL solution is added in the amount of 10 milliliters per liter of *M. bovis* culture(s). The pH of the BPL-*M. bovis* suspension is maintained between 6.5 and 7.8, by adding sodium hydroxide as needed. The suspension is warmed to room temperature and continuously agitated for 24 hours. The cells are concentrated by centrifugation at 8,000 g or by ultrafiltration.

D. Adjuvanting and Formulation of Vaccine

Adjuvanting and final formulation of bulk concentrated inactivated *M. bovis* cultures were done concurrently as described in following protocol:

1) Determine the final volume batch quantity desired based upon 2 milliliters per dose. Quantity of each ingredient to be added is then calculated as described in steps 2 through 5.

2) Dispense an amount of inactivated *M. bovis* cell concentrate necessary to contain a protective dose quantity sufficient for the total number of doses being formulated, based on the cell counts determined in the live culture.

3) Dilute the inactivated *M. bovis* cell concentrate with 0.85% saline solution sufficient to bring the batch to the final desired volume (following addition of adjuvant components)

4) Adjust pH to 6.0 to 6.5 using a 10 normal hydrochloric acid solution.

5) Add an amount of 2% aluminum hydroxide solution to yield a final formulated concentration of 8% to 16%; incubate for 24 hours.

6) Using 10 N sodium hydroxide solution, readjust the pH to 7.2 to 7.4

7) Emulsify mineral oil adjuvant with the diluted aluminum hydroxide-absorbed inactivated *M. bovis* cells with an amount sufficient to yield 4% to 12% in the final formulation.

Example 3

Preparation of Vaccine against *M. bovis* Biotypes A, B and C

A *Mycoplasma bovis* vaccine was prepared containing antigen from 3 biotypes; A, B and C. The process for preparation of vaccine from line was the same as described for Example 2 above. Immunogenic components from biotypes A, B and C were combined after inactivation of selected quantities of pure cultures of each biotype.

Example 4

Preparation of Vaccine Against *M. bovis* Biotypes A, B, C and *M. alkalescens*

Five lung and ear isolations were obtained from necropsied calves. Using indirect immunofluorescence, the isolates were identified by Biomune as:

S99-0052—*M. bovis*—Lung
S99-0052—*M. bovis*—Ear
S99-0053—*M. bovis*—Lung
S99—0053-*M. alkascens*—Lung.

Cultures were passaged 4× in Hayflicks modified liquid media with characterization and preparation of pure cultures.

Samples of cultures from isolates S99-0052 and S99-0053 were further characterized and were determined to be pure *M. bovis* and *M. alkalescens* by an independent laboratory. Identity of isolate S99-0053 as *M. alkascens* was confirmed by further testing.

Two groups of isolates were further characterized. Cytotoxicity cell culture bioassays and PCR fingerprinting were performed. These assays confirmed the identification of the cultures, to be used for vaccine production, to be pure *M. bovis* and *M. alkalescens,*

From the isolated *Mycoplasma*, a vaccine containing antigens from *M. bovis* biotypes A, B, C and antigens from *M. alkalescens* was prepared using the protocol described earlier.

Example 5

Field Trial of Vaccine Against *M. bovis* Biotype A

Efficacy of an inactivated vaccine of this invention specific for *M. bovis* biotype A was determined under field conditions at a site with an endemic mycoplasma mastitis infection in the herd. An active field challenge was confirmed, based on a historical review of cull cow losses due to *M. bovis*, farm site *M. bovis* environmental isolation records, cultural isolation of *M. bovis* from clinical mastitis cases in the non-vaccinated animals, and isolation of *M. bovis* from dairy bulk tanks. Laboratory tests confirmed the identity of these isolations.

The dosage and regime protocol for field vaccinations were as follows:

Administration: 2 milliliter dose of an oil emulsion adjuvanted *M. bovis* vaccine; subcutaneous injection in neck region Regime: 3 doses of vaccine For lactating cows:

1st Vaccination at Dry Off (End of Lactation Cycle)

2nd Vaccination 2 to 3 Weeks Following $1^{st}$ injection     3rd Vaccination 2 to 3 Weeks Following $2^{nd}$ injection For heifers:

The 3 doses are spaced 2-4 weeks apart prior to calving. Preferably, the last dose is administered at least 10 days prior to calving and the start of the lactation cycle.

Comparative results were used to measure efficacy of the vaccine. Samples taken from all animals presenting with clinical mastitis were cultured by an independent laboratory to monitor the absence or presence of *Mycoplasma bovis* infection of the mammary gland. Field evaluations were made by comparing clinical incidence of mastitis caused by *Mycoplasma bovis* following herd vaccination to the base line herd incidence prior to vaccination. Results were as follows:

Pre Vaccination Base Line Incidence:

155 confirmed positive clinical *Mycoplasma bovis* infections Post Vaccination Herd Incidence:

$1^{st}$ year following vaccination:

24 confirmed positive clinical *Mycoplasma bovis* infections     $2^{nd}$ year following vaccination:

1 confirmed positive clinical *Mycoplasma bovis* infection No injection reactions were observed. No inflammatory udder reactions were observed.

Animals were also evaluated for serological response using serum collected from individual animals prior to and following the $2^{nd}$ vaccination. A direct ELISA was performed, with the following results for selected animals:

| Animal ID: | O.D. values | |
|---|---|---|
| | Pre-vaccination | Post-vaccination |
| 82651 | .093 | .313 |
| 82759 | .189 | .693 |
| 61043 | .135 | .273 |
| 3219 | .198 | .586 |
| 83550 | .495 | 1.733 |
| 9296 | .289 | 1.553 |

An immune response is indicated when the post-vaccination values exceed the pre-vaccination values by at least 2 fold.

Example 6

Field Trial of Vaccine Against *M. bovis* Biotypes A, B and C

In the $3^{rd}$ calendar year of the trial described in Example 5, 200 replacement cows were introduced into the herd; 100 at the same site (Site 1) as for Example 5 and 100 into a second related site located in the same geographical area (Site 2). Neither subset of replacement cows were quarantined prior to being introduced to their respective groups. Within 2 months, serious problems with *Mycoplasma* mastitis were reported at both Sites 1 and 2 by personnel at each site.

Testing of all cows at both sites, approximately 4,000 animals altogether, revealed the presence of 22 animals infected with *M bovis*. Initial screening of all animals was accomplished by culturing pooled milk samples (16 cows/sample). When pooled samples were identified as positive for *M. bovis* by culturing milk, all animals in positive groups were tested individually. Three independent studies confirmed isolation of "bovis species" and identification of the three different biotypes (A, B and C) of *M. bovis* was made by PCR fingerprinting. The PCR fingerprinting was carried-out as described above in Example 1.

A vaccine was prepared using antigen from 3 biotypes of *M. bovis* (A, B and C) as described in Example 3 above and was used to vaccinate cattle at both Site 1 and Site 2 according to the regime described in Example 5. Vaccinations began in mid-September, 1999. The incidence of *Mycoplasma* mastitis was monitored by independent laboratory testing for the presence of *Mycloplasma* in any animal determined by farm personnel to have mastitis.

Following vaccination of a significant portion of the herd at Site 1 and Site 2, the incidence of mycoplasma was greatly reduced. From Jan. 1, 2000 to Jul. 18, 2000, there were only 10 animals reported positive for *Mycoplasma bovis* at each site. This reduction in the incidence of *Mycoplasma* positive mastitis cows was regarded as a significant reduction by the operators of Sites 1 and 2. A breakdown of the incidence during Calendar year 2000 is as follows:

| | Site 1 | Site 2 |
|---|---|---|
| January | 1 | 2 |
| Febuary | 1 | 1 |
| March | — | 3 |
| April | 3 | 1 |
| May | 1 | 2 |

-continued

| | Site 1 | Site 2 |
|---|---|---|
| June | 1 | — |
| July | 3 | — |

Example 7

Field Trial of Vaccine against *M. bovis* Biotypes A, B, C and *M. alkalescens*

A vaccine prepared according to Example 4 comprising antigen from *M. bovis* biotypes A, B, C and *M. alkalescens* was used to vaccinate calves at a large 17,000 head-calf raising facility. It has been determined by the site's operators that *Mycoplasma* is a major respiratory problem. Sample bleedings and serological evaluation prior to initiation of the trial indicated that approximately 50% of calves received are serologically negative as determined by direct ELISA bioassay.

Calves selected for the trial were bled and identified with numbered tags on Oct. 19, 1999. Serum was immediately collected. Each of the calves was given the normal treatment regime for newborn cattle arriving at the site (colostrum, etc.). In addition, the calves were vaccinated three times with 2 mL of the vaccine prepared in Example 4. Vaccine was administered approximately every 7 days for the first 3 weeks. On Nov. 22, 1999, serum samples were taken from the 36 calves remaining of the original 50. On Dec. 21, 1999, serum samples were taken from 35 of the 36 calves remaining of the original 50 (one calf could not be located).

Response to vaccination was monitored using the ELISA bioassay used earlier to determine the serological status of calves at the site prior to initiating the trial. A representative-random sample of calves (16) which had been serologically negative at day zero was monitored at day zero, post $2^{nd}$ vaccination and post $3^{rd}$ vaccination. A 7-fold increase in the immunological response over their pre-vaccinated status was realized in the animals following the vaccination procedure. This is believed to be a significant response and the vaccine's efficacy was confirmed by the fact that the vaccinated animals performed well as measured by days to market and rate of gain, both important indicators of a calf's health and well-being.

Example 8

Field Trial of Vaccine Against *M. bovis* Biotype B

Biotype B was isolated from a 1200 cow Jersey dairy herd experiencing *Mycoplasma* mastitis infections in the herd. A vaccine against Biotype B was prepared as described in Example 2 and used in a manner consistent with the vaccination regime previously described. Following the initiation of the vaccination regime for the herd in February, 2000, a veterinarian monitored the herd for the incidence of *M. bovis*. The dairy reported in September 2000 that there were no confirmed cases of *Mycoplasma* in vaccinated animals, despite the continued challenge from the presence of confirmed, infected nonvaccinated animals. As of September, approximately 50% of the herd had been vaccinated. No unfavorable reactions resulting from the vaccine's use have been reported.

Example 9

Field Trial of Vaccine Against *M. bovis* Biotype C

Biotype C was isolated from a cultured isolate derived from a Holstein dairy herd of approximately 400 animals. This herd had been experiencing *Mycoplasma* mastitis infections and had been experiencing positive bulk milk tanks for the year prior to May, 1999. In March, 1999, thirteen cows had been identified as positive for *Mycoplasma bovis* infection. A vaccine specific for biotype C was made as described in Example 2 and was used in a manner consistent with the vaccination regime previously described. The owner and herd health veterinarian monitored performance of the vaccine. There have been no reported clinical mastitis events in vaccinated animals. No unfavorable reactions in animals receiving the product have been reported.

What is claimed is:

1. A vaccine composition comprising
   (a) an immunologically effective amount of (i) at least two inactivated *Mycoplasma bovis* biotypes and (ii) an inactivated *Mycoplasma alkalescens*, wherein said immunologically effective amount is protective in a vaccinate against Bovine Respiratory Disease resulting from *Mycoplasma* infection;
   (b) an adjuvant; and
   (c) a pharmaceutically effective carrier.

2. The vaccine of claim 1 further comprising antigenic material of viruses or microorganisms other than *Mycoplasma bovis* and *Mycoplasma alkalescens* known to be bovine pathogens.

3. The vaccine of claim 2 where the antigenic material is from *Staphylococcus aureus, Pasteurella hemolytica, Pasteurella multocida, Haemophilus somnus,* Bovine Respiratory Syncytial Virus, Bovine Diarrhea Virus, *E. coli* or Infectious Bovine Rhinotrachial Disease.

4. The vaccine of claim 1 where the adjuvant is an aluminum hydroxide-oil emulsion; a mineral, vegetable, or fish oil-water emulsion; a water-oil-water emulsion; incomplete Freund's adjuvant; *E. coli* J5; dextran sulfate; iron oxide; sodium alginate; Bacto-Adjuvant; a synthetic polymer; Carbopol; a poly-amino acid; a co-polymer of amino acids; saponin; carrageenan; REGRESSIN®; N,N-dioctadecyl-N'-N'-bis(2-hydroxyethyl) propanediamine; a long chain polydispersed β(1,4) linked mannan polymer interspersed with O-acetylated groups; deproteinized cell wall extracts from a non-pathogenic strain of *Mycobacterium;* mannite monooleate; paraffin oil; or muramyl dipeptide.

5. The vaccine of claim 1 where the respiratory disease is respiratory pneumonia.

6. The vaccine of claim 1 where the at least two inactivated *Mycoplasma bovis* biotypes are genetically different as determined by an analysis of DNA or RNA from the biotypes.

7. The vaccine of claim 6 wherein the analysis is by PCR fingerprinting, analysis of ribosomal RNA, or analysis of DNA polymorphisms.

8. The vaccine of claim 7 wherein the analysis is by PCR fingerprinting.

9. The vaccine of claim 8 wherein the PCR fingerprinting uses arbitrarily chosen primers.

10. The vaccine of claim 9 wherein the PCR fingerprinting uses as primers 5' NNN NCG NCG NCA TCN GGC 3' (SEQ ID NO:1) and 5' NCG NCT TAT CNG GCC TAC 3' (SEQ ID NO:2).

11. The vaccine of claim 1 wherein the at least two *Mycoplasma bovis* biotypes have been identified as being different biotypes by a process comprising:
    (a) isolating DNA from the biotypes;
    (b) amplifying the DNA by PCR;
    (c) separating the amplified DNA by gel electrophoresis; and
    (d) comparing the resulting patterns from the gel electrophoresis to identify the different biotypes.

* * * * *

UNITED STATES PATENT AND TRADEMARK OFFICE
CERTIFICATE OF CORRECTION

| | | |
|---|---|---|
| PATENT NO. | : 7,416,734 B2 | Page 1 of 1 |
| APPLICATION NO. | : 10/825391 | |
| DATED | : August 26, 2008 | |
| INVENTOR(S) | : Joan D. Leonard et al. | |

It is certified that error appears in the above-identified patent and that said Letters Patent is hereby corrected as shown below:

On the Title Page, Item (62) should read

Related U.S. Application Data

(62)   Division of application No. 10/726,029, filed on Dec. 1, 2003, which is a division of application No. 09/708,352, filed on Nov. 8, 2000.

Signed and Sealed this

Eleventh Day of November, 2008

JON W. DUDAS
*Director of the United States Patent and Trademark Office*

UNITED STATES PATENT AND TRADEMARK OFFICE
CERTIFICATE OF CORRECTION

PATENT NO.        : 7,416,734 B2  
APPLICATION NO.   : 10/825391  
DATED             : August 26, 2008  
INVENTOR(S)       : Joan D. Leonard et al.

Page 1 of 1

It is certified that error appears in the above-identified patent and that said Letters Patent is hereby corrected as shown below:

Column 1, line 5, change "Dec. 2, 2003" to -- Dec. 1, 2003 --;

Column 2, line 67, change "phenyl" to -- phenol --; and

Column 6, line 28, change "$10^9$M." to -- $10^8$M. --.

Signed and Sealed this

Twenty-eighth Day of July, 2009

JOHN DOLL  
*Acting Director of the United States Patent and Trademark Office*

SEQUENCE LISTING

```
<160> NUMBER OF SEQ ID NOS: 2

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence:/Note =
      synthetic construct
<220> FEATURE:
<221> NAME/KEY: misc_feature
<222> LOCATION: (0)..(0)
<223> OTHER INFORMATION: N is deoxyinosine

<400> SEQUENCE: 1
nnnncgncgn catcnggc                                                   18

<210> SEQ ID NO 2
<211> LENGTH: 18
<212> TYPE: DNA
<213> ORGANISM: Artificial Sequence
```

```
-continued
<220> FEATURE:
<223> OTHER INFORMATION: Description of Artificial Sequence:/Note =
      synthetic construct
<220> FEATURE:
<221> NAME/KEY: misc_feature
<222> LOCATION: (0)..(0)
<223> OTHER INFORMATION: N is deoxyinosine

<400> SEQUENCE: 2
ncgncttatc nggcctac                                                     18
```